United States Patent [19]
Shakoor

[11] Patent Number: 5,921,243
[45] Date of Patent: Jul. 13, 1999

[54] DEVICE FOR APPLYING THERAPY TO A FOOT

[76] Inventor: Stacy M. Shakoor, 26 Sassafras La., San Ramon, Calif. 94583

[21] Appl. No.: 08/937,088

[22] Filed: Sep. 24, 1997

[51] Int. Cl.$^6$ ..................................................... A61F 5/37
[52] U.S. Cl. .............................. 128/882; 602/5; 602/14; 607/111
[58] Field of Search .................... 128/846, 881, 128/882; 602/5, 14, 23, 27; 607/108–112, 114

[56] References Cited

U.S. PATENT DOCUMENTS

| | | | |
|---|---|---|---|
| 3,717,145 | 2/1973 | Berndt | 607/112 |
| 4,092,982 | 6/1978 | Salem | 607/112 |
| 5,409,500 | 4/1995 | Dyrek | 607/111 |
| 5,591,221 | 1/1997 | Owens | 607/112 |
| 5,713,837 | 2/1998 | Grim | 602/27 |

*Primary Examiner*—Michael A. Brown
*Attorney, Agent, or Firm*—Flehr Hohbach Test Albritton & Herbert LLP

[57] ABSTRACT

A device for applying therapy to a human foot having a plantar and a dorsum. The device includes a flexible member adapted to extend around the plantar and dorsum of the foot. The flexible member is formed from a flexible material and has at least one first pouch formed integral therewith for engaging a substantial portion of the plantar of the foot and at least one second pouch formed integral therewith for engaging a substantial portion of the dorsum of the foot. Each of the at least one pouches has a liquid therein for applying heating or cooling to the foot.

22 Claims, 7 Drawing Sheets

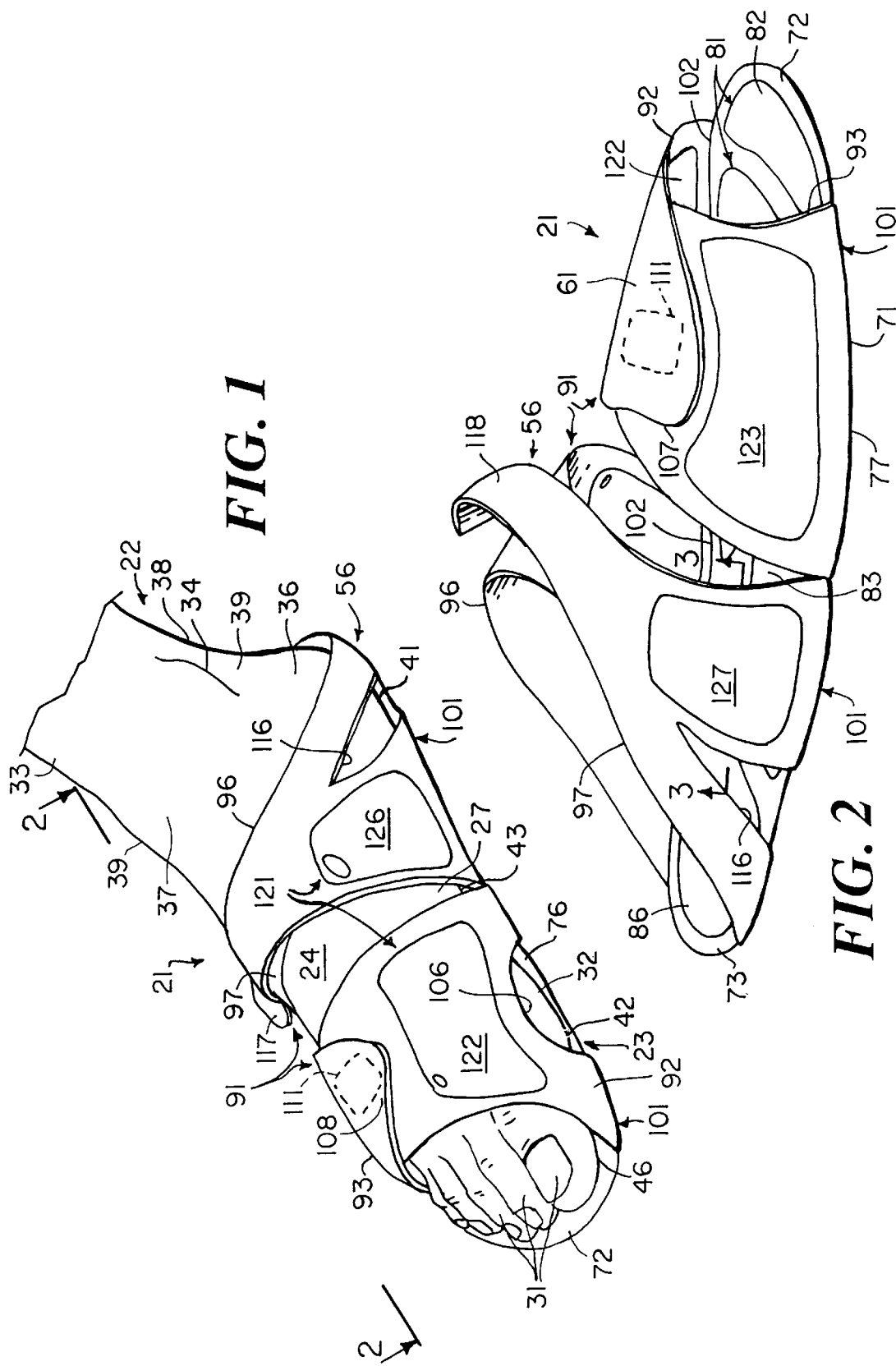

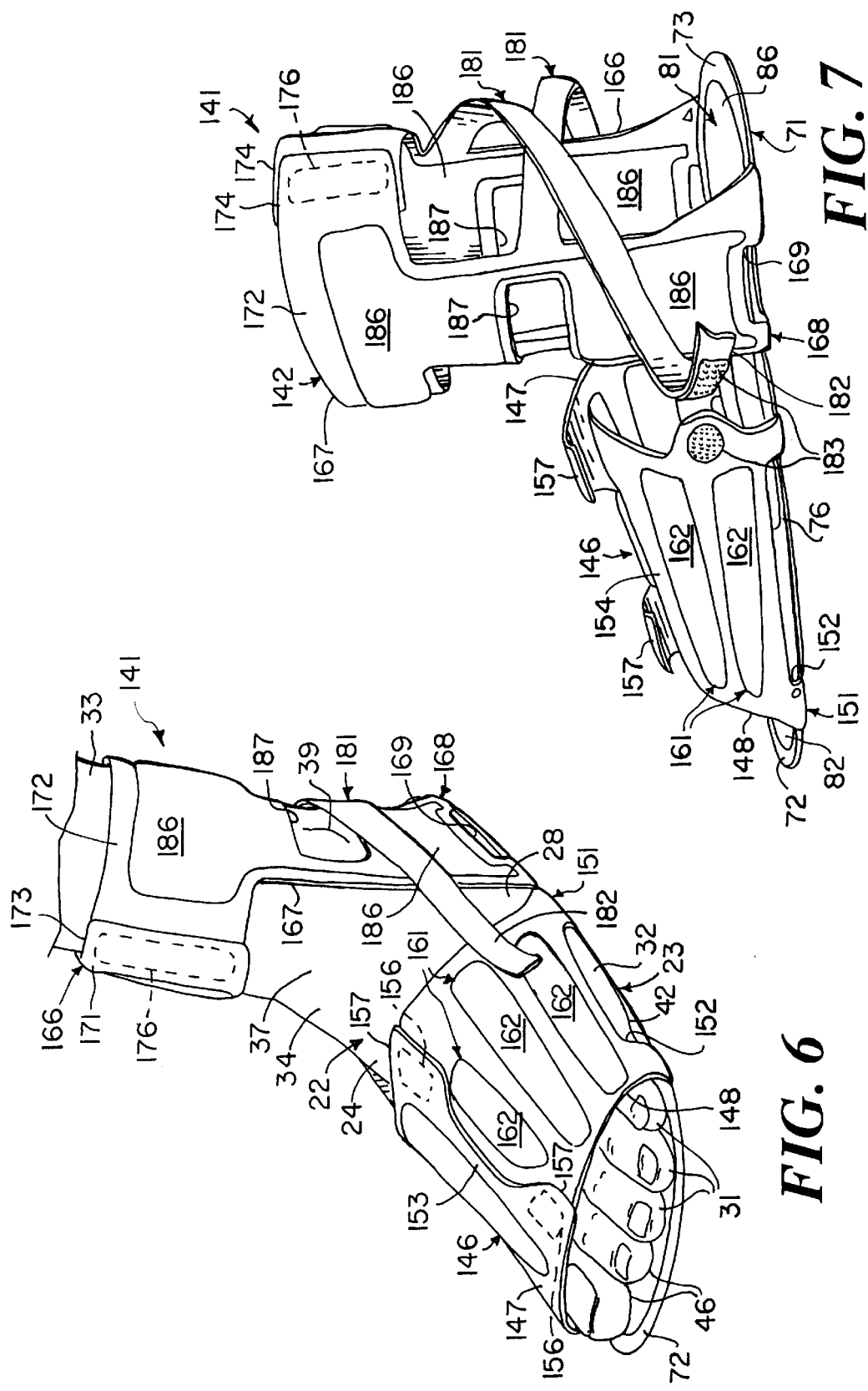

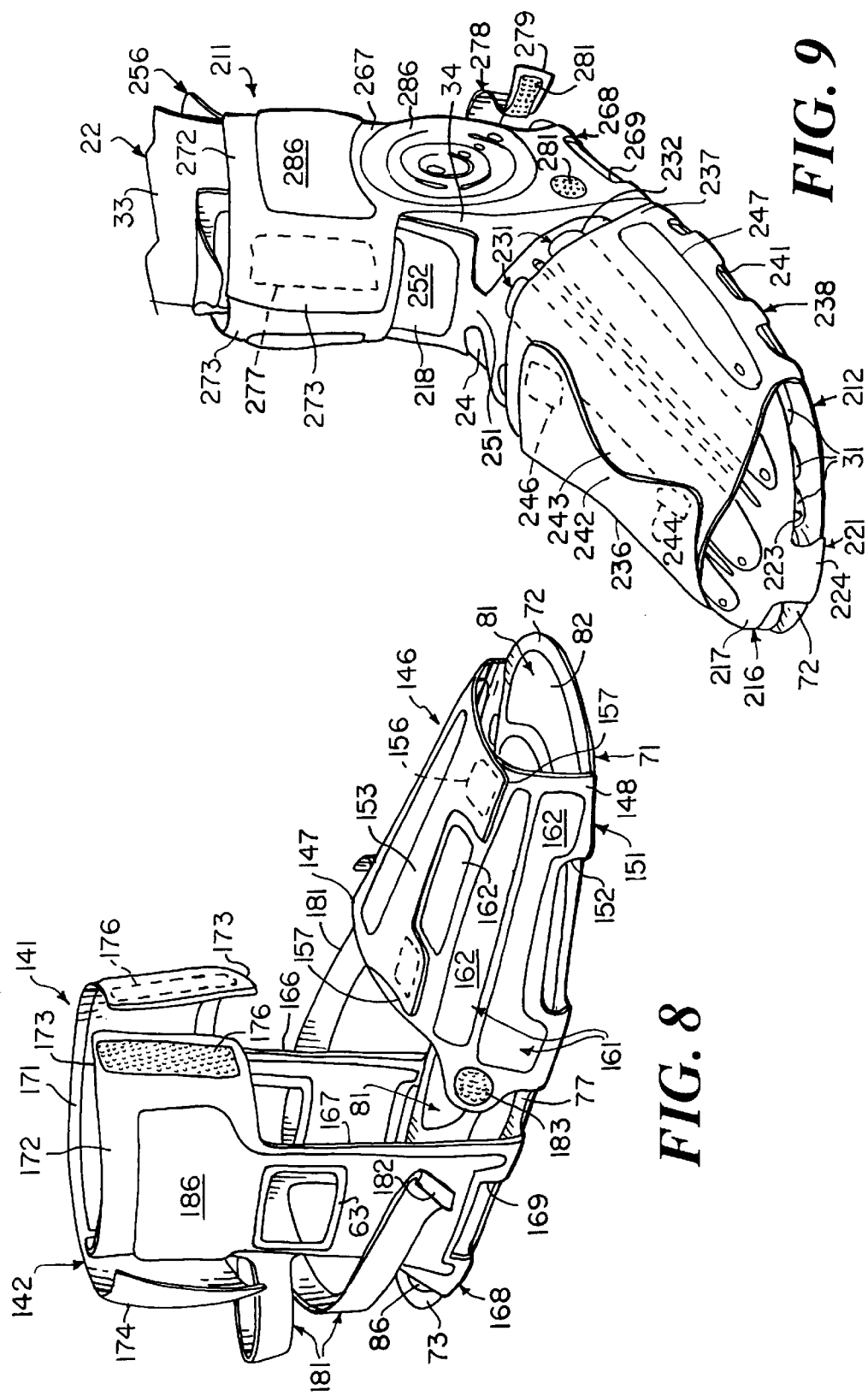

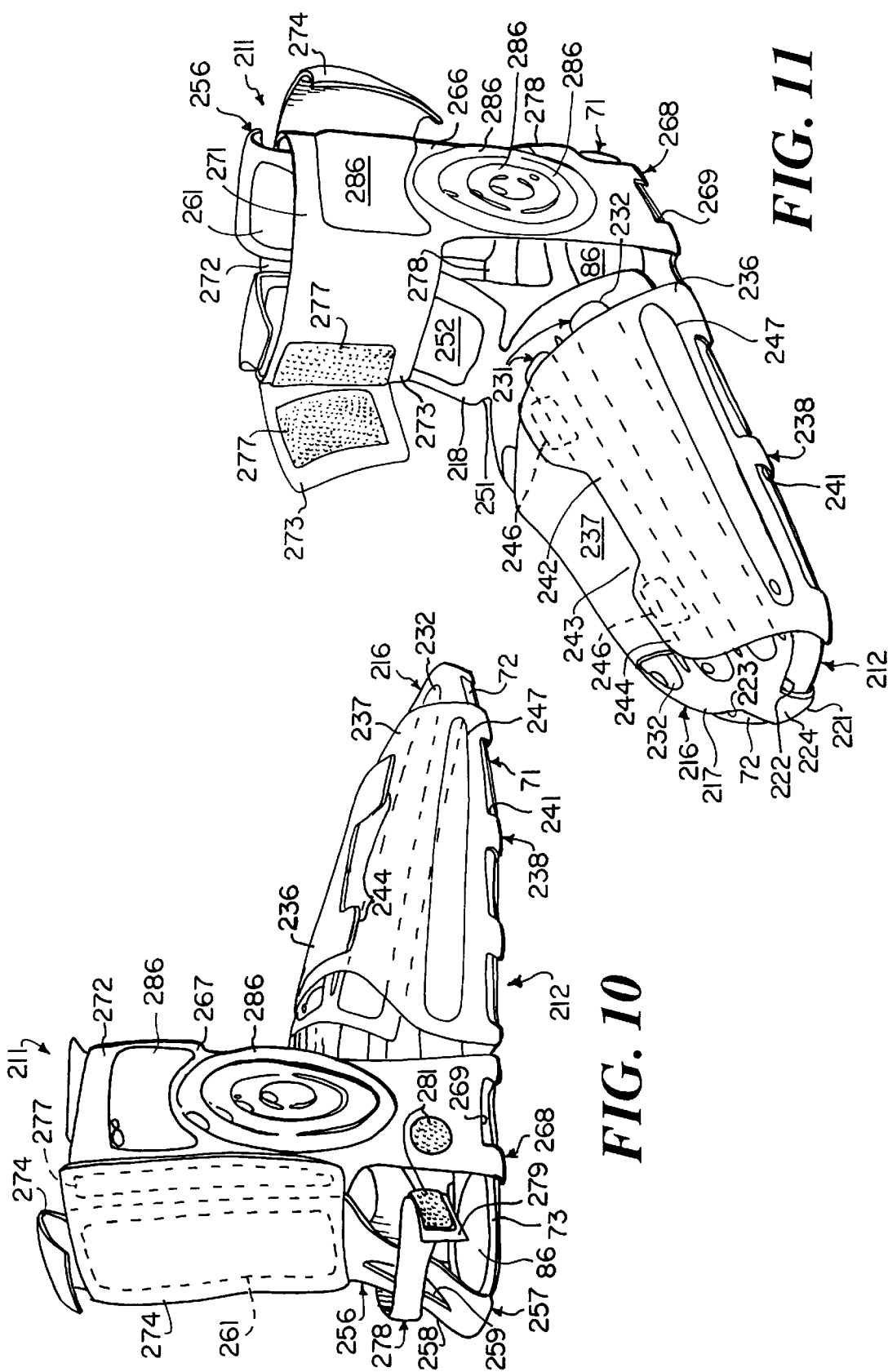

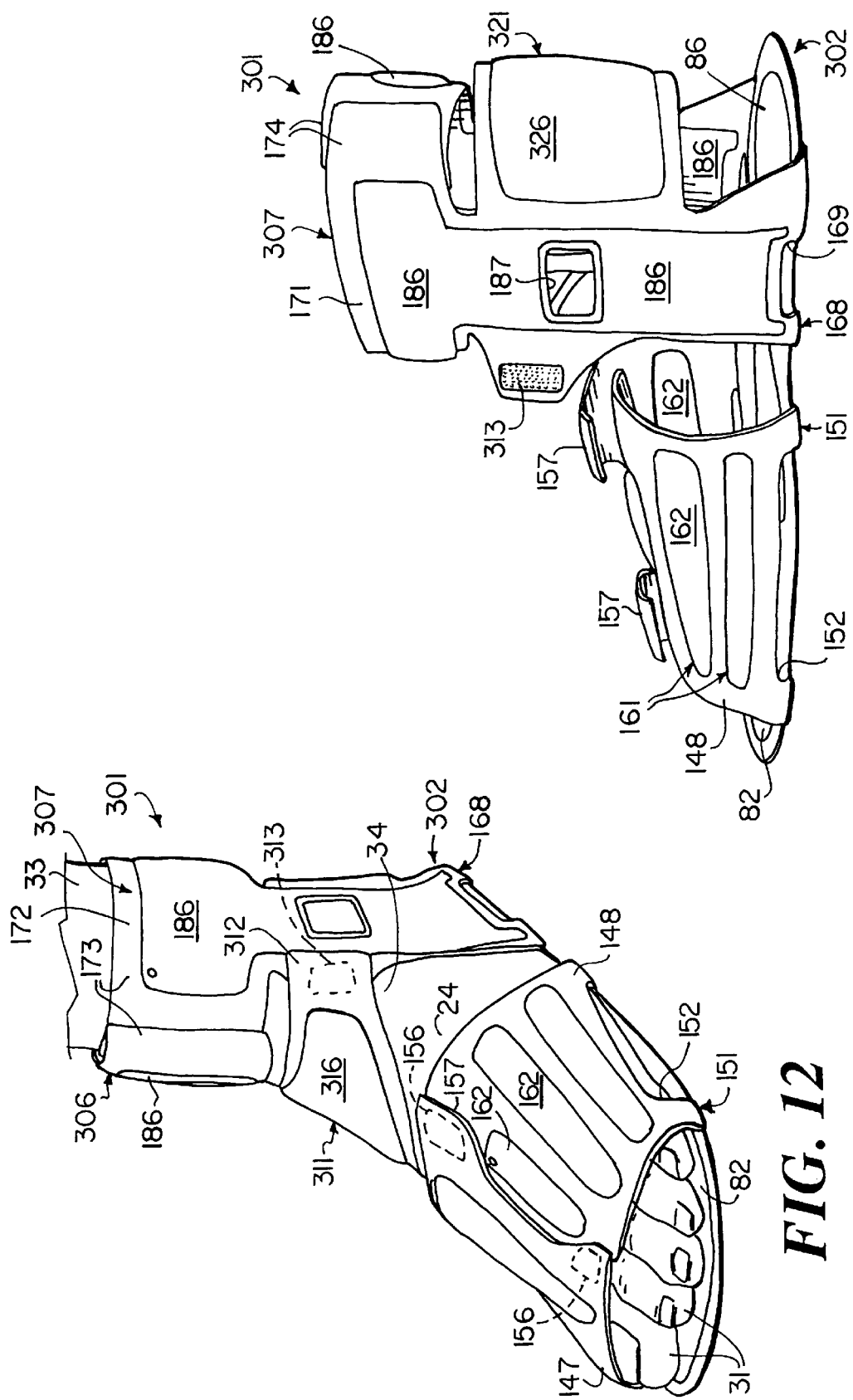

DEVICE FOR APPLYING THERAPY TO A FOOT

This invention pertains generally to therapeutic devices for humans and, more particularly, to therapeutic devices for the human foot.

It is often desirable to apply hot or cold treatments to the human foot to reduce swelling or pain and induce healing. Current methods for applying hot or cold to the foot include immersing the foot in water or ice and wrapping hot or cold packs or liquid containers around the foot. Another current treatment method is home made ice packs. These methods usually require the user to have the foot in an upright position resting on the ground. Current devices attachable to the foot are typically not done so with ease. These devices are not made for specific use on the foot and typically do not conform to the foot. As can be seen, there is a need for a new and improved device for applying hot or cold to the human foot which overcomes the aforementioned disadvantages.

In general, it is an object of the present invention to provide a device which is readily attachable to a foot for applying hot or cold to the foot.

Another object of the invention is to provide a device of the above character which applies hot or cold to the plantar of the foot.

Another object of the invention is to provide a device of the above character which applies hot or cold to the dorsum of the foot.

Another object of the invention is to provide a device of the above character which slips onto the foot.

Another object of the invention is to provide a device of the above character which has a sole having the shape of a foot.

Another object of the invention is to provide a device of the above character which is conformable to the foot.

Another object of the invention is to provide a device of the above character which is adjustable to changes in the shape of the foot.

Another object of the invention is to provide a device of the above character which is readily collapsible for storage.

Another object of the invention is to provide a device of the above character which applies hot or cold to the ankle joint.

Additional objects and features of the invention will appear from the following description from which the preferred embodiment is set forth in detail in conjunction with the accompanying drawings.

FIG. 1 is a perspective view of a device for applying therapy to a foot of the present invention on a right foot of a human.

FIG. 2 is a perspective view of the device of FIG. 1, removed from the right foot, taken along the line 2—2 of FIG. 1.

FIG. 6 is a perspective view of another embodiment of a device for applying therapy to a foot of the present invention on a left foot of a human.

FIG. 7 is a perspective view of the device of FIG. 6 removed from-the left foot.

FIG. 8 is a perspective view of a device similar to the device of FIG. 6 for a right foot of a human.

FIG. 9 is a perspective view of a further embodiment of a device for applying therapy to a foot of the present invention for a left foot of a human.

FIG. 10 is a perspective view of a device similar to the device of FIG. 9 for a right foot of a human.

FIG. 11 is another perspective view of the device of FIG. 10.

FIG. 12 is a perspective view of yet another embodiment of a device for applying therapy to a foot of the present invention, substantially similar to the device of FIGS. 6–8, on a left foot of a human.

FIG. 13 is a perspective view of the device of FIG. 12 removed from the left foot.

Figure 3:
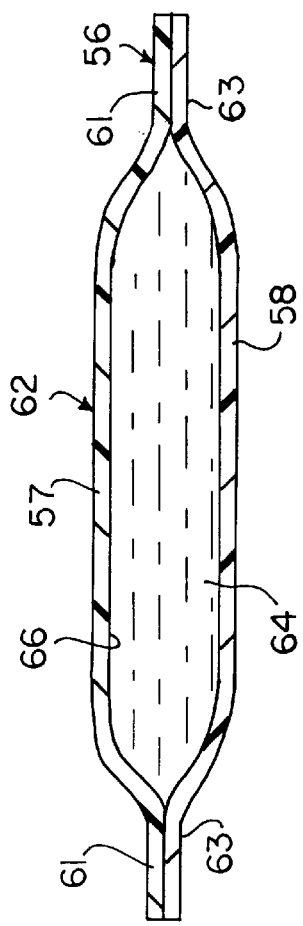
FIG. 3 is a perspective view, similar to FIG. 1, of the device of FIG. 1 removed from the right foot.

In general, a device for applying therapy to a human foot having a plantar and a dorsum is provided. The device includes flexible means adapted to extend around the plantar and dorsum of the foot. The flexible means is formed from a flexible material and has first pouch means formed integral therewith for engaging a substantial portion of the plantar of the foot and second pouch means formed integral therewith for engaging a substantial portion of the dorsum of the foot. Each of the pouch means has at least one fluid tight pouch and a liquid therein for applying heating or cooling to the foot.

More in particular, device 21 of the present invention is for applying hot or cold therapy to a human foot 22 having a volar or plantar 23 forming the bottom of the foot and a dorsum 24 forming the top of the foot. The longitudinally-extending foot 22 has inner and outer sides 27 and 28 extending between the plantar 23 and the dorsum 24. A plurality of five longitudinally-extending toes 31 form the front of the foot and extend forwardly from a metatarsal joint 32. Foot 22 is connected to an ankle 33 of a leg at the tarsus or ankle joint 34 disposed above the heel 36 of the foot. Ankle joint 34 has a front 37 and a back 38 and opposite inner and outer sides 39 adjoining the front and back of the ankle joint. Plantar 23, as shown most clearly in FIG. 4, includes a heel pad 41 and a ball pad 42. An arch 43 extends between the heel and ball pads 41 and 42 at the inner side portion of the foot. A central pad 44 extends alongside the arch 43 on the outer side portion of the foot between the pads 41 and 42. The bottoms of toes 31 collectively form a toe pad 46.

Figure 4:
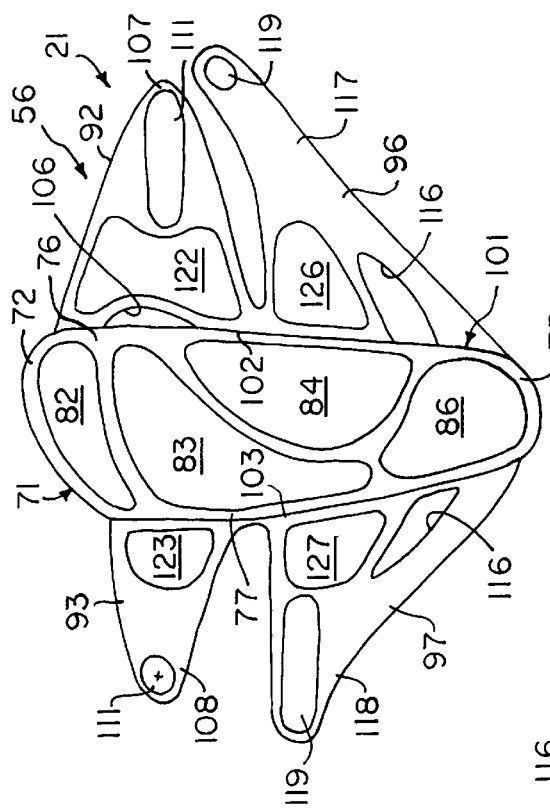
FIG. 4 is a top plan view of the device of FIG. 1.
Figure 5:
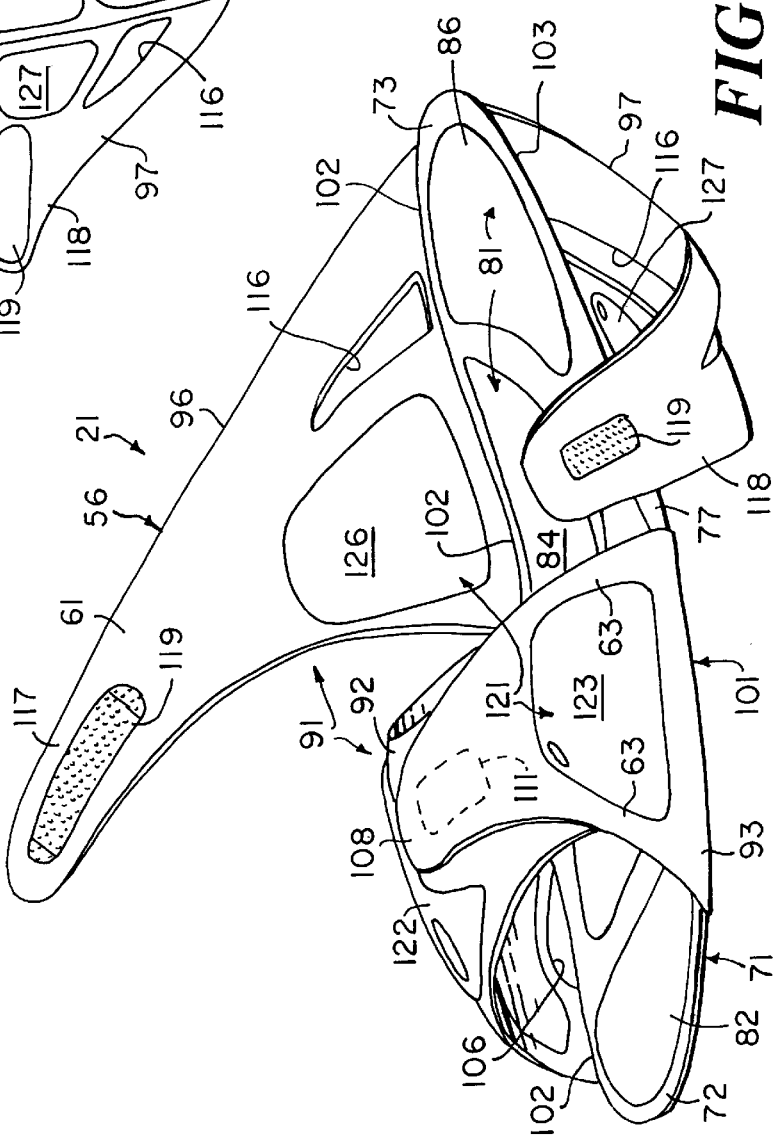
FIG. 5 is a perspective view of a device similar to the device of FIG. 1 for a left foot of a human.

Device 21 is formed from a single flexible means or member 56 made from any suitable flexible material such as plastic (see FIGS. 1–5). A device 21 for a right foot is shown in FIGS. 1 and 2. A device 21 for a left foot is shown in FIG. 5. Specifically, the planar flexible member 56 is formed from a first or upper sheet 57 of plastic material and a second or lower sheet 58 of plastic material. Thin sheets 57 and 58 each have the same pattern and are each made from any suitable liquid impermeable material such as clear polyvinyl chloride (PVC) or polyurethane. Sheets 57 and 58 are secured together by any suitable means such as being heat sealed together at heat sealed means or portions 61.

Pouch means in the form of at least one and as shown a plurality of pouches 62 is formed integral with flexible member 56. As shown most clearly in FIG. 3, each pouch 62 is formed by upper and lower sheets 57 and 58 each having a thickness ranging from five to fifteen millimeters and preferably ranging from six to ten millimeters. Upper and lower sheets most preferably have thicknesses of seven and ten millimeters, respectively. Heat sealed portion 61 forms the outer periphery or boundary 63 of each pouch 62. A fluid in the form of liquid 64 is disposed within the internal chamber 66 of each pouch 62 for applying hot or cold therapy to foot 22. Liquid or gel 64 can be of any suitable type capable of retaining heat or cold for at least twenty minutes. Suitable liquids for use in pouches 62 are aqueous polymeric gels. Liquid 64 is of low acute and chronic toxicity and causes no more than minimal skin or eye irritation in accidental spills. It is preferred that liquid 64 be colored so as to add to the aesthetics of device 21.

Flexible member 56 includes a sole portion or sole 71 adapted for engaging plantar 23. Sole 71 has a shape or profile that, when viewed in plan, generally conforms to the shape of foot 22. As such, the generally planar sole 71 underlies the entire plantar 23 of foot 22. Longitudinally-extending sole 71 has opposite front and rear end portions 72 and 73. First and second spaced-apart side portions in the form of inner side portion 76 and outer side portion 77 extend longitudinally of sole 71 between end portions 72 and 73.

Flexible member 56 includes first pouch means 81 for engaging a substantial portion of plantar 23 and preferably at least approximately 70% of the plantar 23. First pouch means includes at least one pouch 62 and, as shown in FIG. 4, includes a plurality of four pouches 62. Front pouch 82 has a shape in plan generally corresponding to toe pad 46. Alternately, front pouch 82 can be a plurality of pouches 61, one for the pad of each of the toes 31. Outer pouch 83 is disposed rearwardly of front pouch 82 and has a shape in plan at least conforming to the shape of ball pad 42. Inner pouch 84 has a shape in plan generally conforming to the shape of arch 43 and rear pouch 86 has a shape in plan generally corresponding to the shape of heel pad 41. Although rear pouch 86 is shown in FIG. 4 as having no inner periphery, an alternate embodiment of the rear pouch 86 can be somewhat toroid in shape and thus have an inner periphery formed from heat sealed portion 61 of the flexible member 56. This inner periphery of the alternate embodiment of rear pouch 86 would be preferably circular in shape. Outer pouch 83 as shown in FIG. 4 extends rearwardly alongside inner pouch 84 to approximately the center of central pad 44 of foot 22. Rear pouch 86 extends forwardly alongside inner pouch 84 so as to underlie at least a portion of central pad 44.

Flexible member 56 is provided with flap means 91 for extending over dorsum 24. In device 21, flap means 91 includes front inner and outer flap members or flaps 92 and 93 and rear inner and outer flap members or flaps 96 and 97 spaced longitudinally behind front flaps 92 and 93. Hinge means 101 is provided for pivotably securing the flaps to sole 71 and includes inner and outer folds 102 provided along the edges of inner and outer side portions 76 and 77 of sole 71.

Front flaps 92 and 93 are connected to opposite side portions 76 and 77 at the front of sole 71 alongside metatarsal joint 32 of foot 22. The front flaps 92 and 93 are each generally triangular in shape. The base of the triangle is secured to sole 71 by hinge means 101. Inner flap 92 has a cutout 106 where the 92 flap joins sole 71 (see FIG. 1). Cutout 106 is generally oblong in shape in the longitudinal direction of sole 71 and is disposed approximately in the center of the base of the flap 92. The cutout 106 is included within the hinge means 101 and enhances the bending of the flap 92 at the inside edge of sole 71.

Flap 92 has a length sufficient to permit the flap to extend at least halfway over the top of dorsum 24 and is formed with a rounded free end portion 107. Similarly, outer flap 93 has a length sufficient to permit the flap 93 to extend at least halfway across the top of dorsum 24 and is formed with a rounded free end portion 108 which extends over rounded end portion 107. Conventional cooperatively interengaging Velcro strips 111 are included within the means carried by flaps 92 and 93 for removably securing together rounded end portions 107 and 108. Strips 111, shown in dashed lines in FIGS. 1, 2 and 5, consist of one strip secured by adhesive or any other suitable means to the outer surface of rounded end portion 107 and another strip 111 similarly secured to the inner surface of rounded end portion 108. It should be appreciated that other means can be provided for removably and temporarily securing together end portions 107 and 108 and be within the scope of the present invention.

Rear flaps 96 and 97 are also triangular in shape and extend rearwardly along side portions 76 and 77 from the rear end of front flaps 92 and 93 to rear end portion 73 of sole 71. Each of flaps 96 and 97 is provided with a cutout 116 which extends upwardly from the base of the flap. Cutouts 116 are aligned longitudinally of sole 71 on the approximate rear third of flaps 96 and 97 and are included in hinge means 101. The rear flaps 96 and 97 taper as they extend from sole 71 to respective rounded free end portions 117 and 118. End portions 117 and 118 each extend at least over the top of dorsum 24 in the vicinity of ankle joint 34 with end portion 118 disposed atop end portion 117. Velcro strips 119, substantially similar to Velcro strips 111, are included within the means carried by flaps 96 and 97 for removably securing end portions 117 and 118 together.

Second pouch means 121 is formed integral with flap means 71 for engaging a substantial portion of dorsum 24 and inner and outer sides 27 and 28 of the foot 22. The second pouch means preferably engages at least approximately 70% of the dorsum 24 and sides 27 and 28. Second pouch means 121 include at least one pouch 62 and as shown includes a plurality of pouches 62. Specifically, each of front flaps 92 and 93 and rear flaps 96 and 97 is provided with at least one pouch having liquid 64 therein. In this regard, front inner and outer flaps 92 and 93 have respective front pouches 122 and 123 extending along the bottom of the flaps. Pouches 122 and 123 extend upwardly on the flaps 92 and 93 to a point below Velcro strips 111 and thus cover a substantial portion of metatarsal joint 32 when mounted on the foot 22. Rear pouches 126 and 127 are respectively provided in rear inner and outer flaps 96 and 97. Rear pouches 126 and 127 are disposed forward of cutouts 116 and extend generally from the bottom of flaps 96 and 97 upwardly over dorsum 24 to a point below Velcro strips 119.

In operation and use, device 21 is mounted on a foot 22 for applying heat or cold to the foot to thus treat such ailments as injured or sore muscles and tendons and plantar fasciitis. Should it be desired to apply cooling to the foot, liquid 64 within pouches 62 is first cooled by any suitable means such as placing device 21 in an ice bucket, refrigerator or freezer. Conversely, if it is desired to apply heating to the foot, liquid 64 is heated by any suitable means such as by placing device 21 in hot water.

Flexible member 56 of device 21 is adapted for extending around the plantar 23 and dorsum 24 of the foot 22. The flexibility of sheets 57 and 58 facilitates placement of the device 21 on the foot. Device 21 is firmly mounted on foot 22 by placing plantar 23 of the foot 22 on sole 71 and respectively securing together front flaps 92 and 93 and rear flaps 96 and 97. Velcro strips 111 and 119 permit the flaps to be adjustably secured to foot 22 so as to accommodate variations in the size of the foot. In addition, device 21 can be provided in various sizes. For example, the length and width of sole 71 can be varied as well as the length and width of flaps 92 and 93 and flaps 96 and 97.

Once device 21 has been so secured to foot 22, the user can freely move foot 22 about without fear of device 21 falling off the foot. Foot 22 having device 21 thereon is easily elevated above the heart of the user when the user is in a seated or reclined position to enhance the therapy to foot 22. The thickness of flexible member 56, and particularly the thickness of lower sheet 58, permits the user to walk with devices 21 mounted on the feet of the user.

First and second pouch means 81 and 121 are sized and shaped to engage a substantial portion of plantar 23 and dorsum 24 when device 21 is mounted on foot 22. Heating or cooling is applied through ball pad 42 to metatarsal joint 32 by means of outer pouch 83. Heel pad 41 and toe pad 46 are treated by means of rear pouch 86 and front pouch 82, respectively. Inner pouch 84 is sized larger in plan and height relative to sole 71 so as to substantially fully engage arch 43. Metatarsal joint 32 is further treated by front pouches 122 and 123 provided in front flaps 92 and 93. Rear pouches 126 and 127 further treat dorsum 24.

Device 21 is easily collapsible for storage and transport by folding flaps 92 and 93 and 96 and 97 flush against sole 71. Flexible member 56 permits the flaps to be folded about sole 71.

The device for applying therapy to the human foot 22 can have other embodiments and be within the scope of the present invention. An alternate device 141 is shown in FIGS. 6–8. The device 141 is shown on a left foot 22 in FIG. 6 and removed from the left foot in FIG. 7. A similar device 141 for use on a right foot is shown in FIG. 8. Like reference numerals are used in FIGS. 6–8 to show like parts of device 141 and device 21. Unitary device 141 is made from a flexible member 142 which is substantially similar to flexible member 56. The flexible member 142 is formed from upper and lower sheets of plastic material substantially similar to sheets 57 and 58 and includes a sole 71.

Flexible member 142 has flap means 146 in the form of front inner and outer flaps 147 and 148 for extending over dorsum 24. Hinge means 151, substantially similar to hinge means 101, serves to pivotably secure front flaps 147 and 148 to sole 71 of device 141. Hinge means 151 includes an elongate cutout 152 provided at the bottom of each flap 147 and 148 where the flap adjoins sole 71. Cutouts 152 are generally centered on the flaps and have a length approximately equal to one-half the width of the flaps. The flaps 147 and 148 each have a substantially constant width which is approximately equal to the distance from the base of the toes 31 to the front 37 of ankle joint 34. Flaps 147 and 148 each have a length so that the flap extends at least over the top or crest of dorsum 24. Hence, flaps 147 and 148 cover substantially the entire dorsum 24. Front flaps 147 and 148 have respective free end portions 153 and 154 and, as discussed above, are sized so that inner end portion 153 overlies outer end portion 154.

Velcro strips 156, substantially similar to Velcro strips 111, are included within the means carried by flaps 147 and 148 for removably securing together end portions 153 and 154. Inner end portion 153 is provided with spaced-apart tabs 157, one tab at the front of end portion 153 and the other tab at the rear of end portion 153. One of strips 156 is secured by any suitable means to the underside of each tab 157 for cooperatively interengaging with another strip 156 adhered to the top surface of outer end portion 154.

Second pouch means 161 formed integral with front flaps 147 and 148 is provided for engaging a substantial portion of dorsum 24 and sides 27 and 28 of the foot 22. The second pouch means 161 preferably engages at least approximately 70% of dorsum 24 and sides 27 and 28. In this regard, each of front flaps 147 and 148 has at least one pouch and as shown a plurality of strip-like pouches 162 extending longitudinally of device 141 and transversely across flaps 147 and 148. Strip-like pouches 162 are spaced apart across the length of flaps 147 and 148.

Device 141 has rear inner and outer flaps 166 and 167 for extending upwardly from sole 71 alongside ankle joint 34. Hinge means 168, substantially similar to hinge means 101, is included for pivotably securing the bases of flaps 166 and 167 to inner and outer side portions 76 and 77 of sole 71. Rear flaps 166 and 167 are thus bendably secured to sole 71 in longitudinally spaced-apart positions from front flaps 147 and 148 and, more specifically, behind the front flaps. Hinge means 168 has at least one elongate cutout 169 extending longitudinally of device 141 and centered on the base of each flap 166 and 167 where the flap is joined to the rear extremity of sole 71.

Rear flaps 166 and 167 each extend upwardly alongside ankle joint 34 to respective free upper end portions 171 and 172. Each of the upper end portions 171 and 172 is provided with a front tab 173 extending at least halfway around the front of ankle 33 and a rear tab 174 extending at least halfway around the rear of the ankle 33. Thus, respective front tabs 173 and respective rear tabs 174 of rear flaps 166 and 167 overlap. Means in the form of Velcro strips 176, substantially similar to Velcro strips 111, are carried by front and rear tabs 173 and 174 for removably securing together upper end portions 171 and 172 of the rear flaps.

Each of rear flaps 166 and 167 is provided with a strip-like strap member or strap 181 which extends from the rear of the flap 166 and 167 around the back of foot 22 above heel 36. Straps 181 each have a free end portion 182 and a length sufficient so that end portion 182 overlaps the rear of the front flap 147 or 148 on the opposite side of sole 71 near the bottom thereof. Means including Velcro strips 183, substantially similar to Velcro strips 111, are included within device 141 for removably securing end portions 182 of the straps to the flaps 147 and 148.

At least one pouch 186 is formed integral with each of rear flaps 166 and 167 for engaging a side 39 of ankle joint 34. Pouch 186 extends approximately the entire length and width of the flap 166 or 167 so as to engage a substantial portion of the side of heel 36, side 39 of ankle joint 34 and the lower end portion of ankle 33. Each of the pouches 186 extends transversely of the top of flap 166 or 167 so as to extend across a portion of each of tabs 173 and 174. A hole 187 is provided in each of pouches 186 for receiving a malleolus of the ankle joint.

In operation and use, liquid 64 within the pouches of device 141 is heated or cooled in the same manner as discussed above with respect to device 21. Thereafter, device 141 can be mounted on a foot 22 by placing the plantar 23 of the foot on the sole 71 of the device 141. Front flaps 147 and 148 are secured over the top of dorsum 24 by means of Velcro strips 156. Rear flaps 166 and 167 are pulled adjacent sides 39 of ankle joint 34 and upper ends 171 and 172 are secured about ankle 33 by Velcro strips 176 on front and rear tabs 173 and 174. Straps 181 are then pulled around the rear of foot 22 and secured to front flaps 147 and 148. The straps 181 assist in retaining rear pouches 186 against the side of ankle joint 34.

Like device 21, device 141 applies heating or cooling to plantar 23 and dorsum 24. In addition, heating or cooling is applied by device 141 to the inner and outer sides 39 of ankle joint 34 and the sides of the heel 36 and the lower end portion of ankle 33.

As can be seen from device 141, the pouch means of the present invention can have one or more pouches of various designs and configurations for covering a substantial portion of the dorsum 24 or other part of foot 22. The amount of heating or cooling applied to the foot 22 by each of the pouch means is dependent upon the amount of liquid 64 in the pouch means, whether the pouch means consists of a single pouch 62 or a plurality of spaced-apart pouches 62.

In a further embodiment of the present invention, a device 211 is provided which can provide heating or cooling to substantially the entire foot 22. Device 211, shown in FIGS. 9–11, has similarities to devices 21 and 141 and like reference numerals have been used to describe like parts of device 211 and devices 21 and 141. A device 211 for a left foot is shown in FIG. 9 and a device 211 for a right foot is shown in FIGS. 10 and 11. Device 211 is a unitary device formed from a single flexible member 212 similar in composition to flexible member 56. Flexible member 212 is formed from upper and lower sheets of plastic material substantially similar to upper and lower sheets 57 and 58. The flexible member 212 has heat sealed portions 61 and pouches 62 provided therein.

A front flap member or flap 216 is provided with a first or dorsal portion 217 and a second or ankle portion 218. Hinge means 221, substantially similar to hinge means 101, is provided for pivotably securing front flap 216 to front end portion 72 of sole 71. Hinge means 221 includes a fold (not shown) substantially similar to folds 102 and 103. Front flap 216 is provided with first and second spaced-apart cutouts 222 and 223 extending along the sides of dorsal portion or flap 217 to form a single thin strip 224 for attaching the center of the flap 216 to the center of front end portion 72.

Dorsal flap 217 is included within the flap means of device 211 for engaging a substantial portion of dorsum 24 of foot 22 and sides 27 and 28 and preferably at least approximately 70% of the dorsum 24 and sides 27 and 28. Second pouch means 231 is formed integral with dorsal flap 217 and includes at least one and as shown a plurality of pouches 62. Specifically, second pouch means 231 consists of a plurality of strip-like pouches 232 extending longitudinally of dorsal flap 217 and spaced apart transversely across the dorsal flap. Dorsal flap 217, and second pouch means 231 therein, extends over the top of toes 31 and metatarsal joint 32 to the rear of dorsum 24 adjacent ankle joint 34.

Inner and outer front flaps 236 and 237 are included within the means of device 211 for securing and holding dorsal flap 217 firmly against dorsum 24. Hinge means 238, substantially similar to hinge means 101, is provided for pivotably securing front flaps 236 and 237 to inner and outer side portions 76 and 77 of sole 71. Hinge means 238 includes at least one and as shown a plurality of two elongate cutouts 241 extending along the base of the flaps longitudinally of and adjacent sole 71 for facilitating bending of the flaps 236 and 237 where the flaps join the sole 71. Each of the front flaps 236 and 237 extends at least over the top of dorsum 24 so that respective free end portions 242 and 243 overlap along the crest of the dorsum. Front inner flap 236 is provided with front and rear tabs 244 substantially similar to tabs 157. Velcro strips 246 or any other suitable means is carried by tabs 247 in the upper service of outer flap 237 for removably securing together end portions 242 and 243. The Velcro strips are substantially similar to Velcro strips 111.

Each of front flaps 236 has at least one strip-like pouch 247 extending along the bottom of the flap longitudinally of device 21 for engaging the sides of foot 22 through cutouts 222 and 223. Pouches 247, together with dorsal pouches 232, serve to engage substantially the entire top of foot 22 for applying heating or cooling thereto.

Ankle portion or flap 218 of front flap 216 is included within the means of device 211 for applying heating or cooking to ankle joint 34. Ankle flap 218 is substantially rectangular in shape and is pivotably coupled to dorsal flap 217 by means of a thin strip 251. Ankle flap 218 extends up ankle 33 to a point above ankle joint 34 and has a width sufficient to extend around the front 37 of the ankle joint. At least one pouch 252 is formed integral with ankle flap 218. Pouch 252 is substantially rectangular in shape and extends across almost the entire length and width of ankle flap 218.

Flexible member 142 includes a rear flap 256 and hinge means 257 substantially similar to hinge means 101 for pivotably coupling rear flap 256 to rear end portion 73 of sole 71. Rear flap 256 is formed with a narrow strip 258 for extending up the back of heel 36. Strip 258 is provided with an elongate cutout 259 extending up the rear flap 256 for facilitating bending of the flap at strip 258. Rear flap 259 has at least one pouch 261 which is generally rectangular in shape. Pouch 261 has a length sufficient to extend up back 38 of ankle joint 34 and a width sufficient to extend across the back 38.

Means for retaining front and rear pouches 252 and 261 against the front 37 and back 38 of ankle joint 34 includes rear inner and outer flaps 266 and 267. Hinge means 268 substantially similar to hinge means 101 is provided for pivotably securing inner and outer flaps 266 and 267 to sole 71 behind front inner and outer flaps 236 and 237. Hinge means 268 includes a cutout 269 which is provided at the base of each flap 266. Cutouts 269 are substantially similar to cutout 169. Inner and outer flaps 266 and 267 extend upwardly from sole 71 and have respective free upper end portions 271 and 272 for securing to the user's leg above ankle joint 34. Each of flaps 266 and 267 has a front tab 273 substantially similar to front tabs 173 and a rear tab 274 which extends rearwardly from the flap 266 or 267. As shown most clearly in FIG. 10, rear tab 274 of rear inner flap 266 extends around the back of ankle joint 34 over rear pouch 261 and overlaps rear tab 274 of rear outer flap 267. Velcro strips 277 or any other suitable means are carried by front and rear tabs 273 and 274 in the manner discussed above for removably securing together upper end portions 271 and 272 about ankle 33. Velcro strips 277 are substantially similar to Velcro strips 111. Tabs 273 and 274 extend over front and rear pouches 252 and 261 and thus serve to position and retain the pouches on the front 37 and back 38 of ankle joint 34.

An elongate, thin strap member or strap 278 extends from the bottom rear of inner flap 266 around rear strip 258 and has an end portion 279 which overlaps the outer surface of outer flap 267. Velcro strips 281 or any other suitable means are carried by end portion 279 and outer flap 267 for removably securing the end portion 279 to the outer flap 267. Velcro strips 281 are substantially similar to Velcro strips 111.

Rear flaps 266 and 267 each include at least one pouch 286 formed integral therein. The pouch 286 on each flap 266 and 267 covers a substantial portion of the side 39 of ankle joint 34 as well as the side of heel 36 and the lower end portion of ankle 33 engaged by the flap.

In operation and use, device 211 is prepared for use in substantially the same manner as discussed above. Thereafter, the device 211 is mounted on a foot in substantially the same manner as device 141. Device 211 provides heating or cooling to the foot in substantially the same manner as device 141 except, in addition, device 211 further provides heating or cooling to the front 37 and back 38 of ankle joint 34 by means of front and rear pouches 252 and 261. Device 211 collapses for storage and transport.

Figure 14:
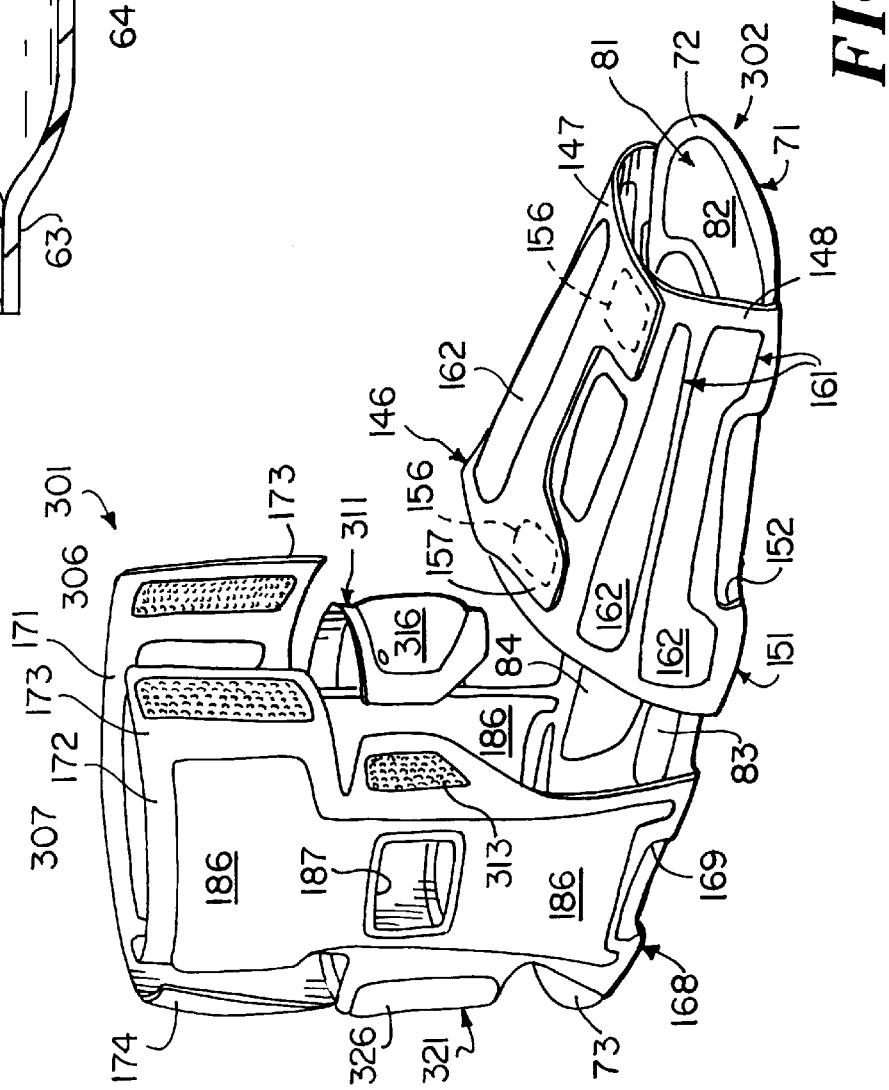
FIG. 14 is a perspective view of a device similar to the device of FIG. 12 for a right foot of a human.

In another embodiment of the present invention, a device 301 for applying heat or cold therapy to a human foot 22 is shown in FIGS. 12–14. Device 301 is substantially similar to device 141 and like reference numerals have been used to describe like parts of devices 141 and 301. A device 301 for a left foot is shown in FIGS. 12 and 13 and a device 301 for a right foot is shown in FIG. 14. Device 301 is a unitary device formed from a single flexible member 302 similar in composition to flexible member 56. Flexible member 302 has upper and lower sheets of plastic material substantially similar to upper and lower sheets 57 and 58. The flexible member 302 has heat sealed portions 61 and pouches 62 provided therein. Sole 71 having first pouch means 81 and inner and outer flaps 147 and 148 having second pouch means 161 are included within device 301.

Device 301 has rear inner and outer flaps 306 and 307 substantially identical to rear inner and outer flaps 166 and 167 except that flaps 306 and 307 do not include straps 181. Instead, rear inner flap 306 includes a front flap 311 formed integral therewith which extends forwardly from the center of flap 306 around the front of ankle joint 34. Front flap 311 has an end portion 312. Conventional cooperatively interengaging Velcro strips 313, substantially similar to Velcro strips 111, are included within the means carried by front flap 311 and the center of rear outer flap 307 for removably securing together end portion 312 and rear outer flap 307. At least one pouch 316 is formed integral with front flap 311 for providing heating or cooling to the front portion of ankle joint 34. Pouch 316 covers substantially the entire front of ankle joint 34 and is somewhat triangular in shape, tapering in width as it extends from rear inner flap 306. Rear outer flap 307 has a rear flap 321 formed integral therewith which extends rearwardly around the back of ankle joint 34 above heel 36. Rear flap 321 has an end portion removably secured to the center of rear inner flap 306 by means of conventional Velcro strips (not shown) substantially similar to Velcro strips 111. At least one pouch 326 is included within rear flap 321. Pouch 326 is rectangular in shape and extends across substantially the entire rear of ankle joint 34.

In the operation and use, device 301 applies heating or cooling to plantar 23 and dorsum 24 and the inner and outer sides 39 of ankle joint 34 in the same manner as device 141. Heating or cooling is applied by device 301 to the front and rear of ankle joint 34. Like device 141, heating or cooling is further provided by device 301 to the sides of heel 36 and to the lower end portion of ankle 33.

It should be appreciated that other embodiments of the device for applying heating or cooling to the foot can be provided which employ one or more features of the devices 21, 141, 211 and 301.

From the foregoing, it can be seen that a device readily attachable to a foot has been provided for applying hot or cold to the foot, including the plantar and dorsum of the foot. The device slips onto the foot and has a sole provided with the shape of a foot. The device is conformable to the foot and is adjustable to changes in the shape of the foot. It is readily collapsible for storage. The device can apply hot or cold to the ankle joint.

What is claimed is:

1. A device for applying therapy to a human foot having a plantar and a dorsum, comprising flexible means adapted to extend around the plantar and dorsum of the foot, the flexible means being formed from a flexible material and including a sole member having first and second opposite sides and at least one upper member extending over the dorsum from the first side to the second side of the sole member, the sole member having a shape in plan corresponding to the plantar of the foot and having at least one first fluid-tight pouch formed integral therewith for engaging a substantial portion of the plantar of the foot, the at least one upper member having at least one second fluid-tight pouch formed integral therewith for engaging a substantial portion of the dorsum of the foot, each of the at least one first and second fluid-tight pouches having a liquid therein for applying heating or cooling to the foot.

2. A device as in claim 1 wherein the flexible means is formed from at least first and second sheets of plastic material, means for bonding together the first and second sheets of plastic material to form the at least one first and second fluid-tight pouches.

3. A device as in claim 2 wherein the bonding means includes heat seal means.

4. A device as in claim 1 wherein the at least one upper member has first and second end portions and means for removably securing together the first and second end portions to attach the flexible means to the foot.

5. A device as in claim 1 for use with a foot having an arch with a shape wherein the at least one first fluid-tight pouch includes a pouch having a shape corresponding to the shape of the arch.

6. A device as in claim 1 wherein the flexible means has hinge means disposed between the at least one first and second fluid-tight pouches.

7. A device as in claim 6 wherein the hinge means includes a fold formed in the flexible means.

8. A device for applying therapy to a human foot having a plantar and a dorsum, the plantar including a heel pad and a ball pad and an arch extending between the heel pad and the ball pad, the toes extending forwardly from the ball pad, comprising at least first and second sheets of flexible plastic, means for bonding together the at least first and second sheets of flexible plastic to form a flexible member, the flexible member including a longitudinally-extending sole portion adapted to engage the plantar, the sole portion being provided with fluid-tight pouch means formed integral with the sole portion for engaging a substantial portion of the plantar including at least the heel pad, the ball pad and the arch, a liquid disposed in the fluid-tight pouch means for retaining heat or cold, the flexible member having flap means for extending over the dorsum and hinge means for pivotably securing the flap means to the sole portion.

9. A device as in claim 8 wherein the flap means is provided with fluid-tight pouch means formed integral therewith for engaging a substantial portion of the dorsum, a liquid disposed in the fluid-tiht pouch means of the flap means for retaining heat or cold.

10. A device as in claim 9 wherein the sole portion has a front end portion, the flap means including a flap and hinge means for pivotably securing the flap to the front end portion.

11. A device as in claim 10 for use with a human having an ankle pivotably connected to the foot at an ankle joint having a front and back, wherein the sole portion has a rear end portion opposite the front end portion, the flap being provided with at least one fluid-tight pouch for engaging the front of the ankle joint, an additional flap and additional hinge means for pivotably securing the additional flap to the rear end portion, the additional flap being provided with at least one additional fluid-tight pouch for engaging the back of the ankle joint, a liquid disposed in the fluid-tight pouch and in the additional fluid-tight pouch for retaining heat or cold.

12. A device as in claim 11 wherein the flap and the additional flap have respective free end portions, means extending around the ankle for retaining the at least one fluid-tight pouch against the front of the ankle joint and the additional fluid-tight pouch against the back of the ankle joints.

13. A device as in claim 8 wherein the sole portion has first and second spaced-apart side portions extending longitudinally of the sole portion, the flap means including first and second flaps having respective free end portions, hinge means for pivotably securing the first and second flaps to the first and second side portions of the sole portion and means for removably securing together the end portions of the first and second flaps.

14. A device as in claim 13 wherein each of the first and second flaps is provided with at least one fluid-tight pouch formed integral therewith, a liquid for retaining heat or cold disposed in the fluid-tight pouches of the first and second flaps.

15. A device as in claim 13 wherein the flap means includes third and fourth flaps having respective free end portions, hinge means for pivotably securing the third and fourth flaps to the first and second side portions of the sole portion spaced longitudinally apart from the first and second flaps and means for removably securing together the end portions of the third and fourth flaps, each of the third and fourth flaps being provided with at least one fluid-tight pouch formed integral therewith, a liquid for retaining heat or cold disposed in the fluid-tight pouches of the third and fourth flaps.

16. A device as in claim 13 for use with a human having an ankle pivotably connected to the foot at an ankle joint having opposite sides, together with third and fourth flaps having respective free end portions, hinge means for pivotably securing the third and fourth flaps to the first and second side portions of the sole portion spaced longitudinally apart from the first and second flaps and means for removably securing together the end portions of the third and fourth flaps around the ankle, each of the third and fourth flaps being provided with at least one fluid-tight pouch formed integral therewith for engaging a side of the ankle joint.

17. A device as in claim 8 for use with a human having a heel on the foot, together with additional flap means for securing the sole portion to the heel of the foot.

18. A device as in claim 8 wherein the fluid-tight pouch means includes a first fluid-tight pouch having a shape in plan generally conforming to the heel pad, a second fluid-tight pouch having a shape in plan generally corresponding to the arch and a third fluid-tight pouch having a shape in plan generally corresponding to the ball pad.

19. A device as in claim 18 for use with a human having toes extending forwardly of the ball pad and collectively forming a toe pad, wherein the fluid-tight pouch means includes a fourth pad having a shape in plan generally corresponding to the toe pad.

20. A device for applying therapy to a human foot having a plantar and a dorsum comprising at least first and second sheets of flexible plastic, means for bonding together the at least first and second sheets of flexible plastic to form a flexible member, the flexible member including a longitudinally-extending sole portion adapted to engage the plantar and at least one flap portion extending up from the sole portion for removably securing the flexible member to the foot, the at least one flap portion being joined to the sole portion at a fold formed in the at least first and second sheets of flexible plastic for facilitating pivoting of the at least one flap portion relative to the sole portion, the at least first and second sheets of flexible plastic forming at least one fluid-tight pouch which engages the foot, a liquid disposed in the at least one fluid-tight pouch for retaining heat or cold.

21. A device as in claim 20 wherein the at least first and second sheets of flexible plastic form at least one first fluid-tight pouch in the sole portion for engaging a substantial portion of the plantar and at least one second fluid-tight pouch in the at least one flap portion for engaging a substantial portion of the dorsum.

22. A device as in claim 21 wherein the sole portion has first and second opposite sides, the at least one flap portion including a first flap portion extending from the first side of the sole portion and a second flap portion extending from the second side of the sole portion, the first and second flap portions being joined to the sole portion at respective first and second folds.

\* \* \* \* \*